US011635064B1

(12) United States Patent
Kartalov et al.

(10) Patent No.: US 11,635,064 B1
(45) Date of Patent: Apr. 25, 2023

(54) MICROFLUIDIC-BASED ARTIFICIAL MUSCLES AND METHOD OF FORMATION

(71) Applicants: California Institute of Technology, Pasadena, CA (US); The Government of the United States of America, as represented by the Secretary of the Navy, Arlington, VA (US)

(72) Inventors: Emil P. Kartalov, Pacific Grove, CA (US); Axel Scherer, Barnard, VT (US)

(73) Assignees: California Institute of Technology, Pasadena, CA (US); The Government of the United States of America, as represented by the Secretary of the Navy, Arlington, VA (US)

( * ) Notice: Subject to any disclaimer, the term of this patent is extended or adjusted under 35 U.S.C. 154(b) by 153 days.

(21) Appl. No.: 17/338,393

(22) Filed: Jun. 3, 2021

Related U.S. Application Data

(63) Continuation of application No. 16/442,092, filed on Jun. 14, 2019, now Pat. No. 11,060,511.
(Continued)

(51) Int. Cl.
*A61F 2/08* (2006.01)
*H02N 1/00* (2006.01)
(Continued)

(52) U.S. Cl.
CPC ............... *F03G 7/06* (2013.01); *A61F 2/08* (2013.01); *A61F 2/70* (2013.01); *A61H 1/02* (2013.01);
(Continued)

(58) Field of Classification Search
CPC ...... F15B 15/103; F15B 15/10; F15B 21/065; F15B 21/06; F15B 2215/305; H02N 1/004; H02N 1/00; H02N 1/002; H02N 1/006; H02N 1/008; H02N 1/06; H02N 1/08; A61F 2/08; A61F 2/70; A61F 2/68; A61F 2/02;
(Continued)

(56) References Cited

U.S. PATENT DOCUMENTS 6,888,715 B2    5/2005   Stevenson et al.
7,679,268 B2    3/2010   Yokoyama et al.
(Continued)

OTHER PUBLICATIONS

Caleb Christianson et al., "Translucent soft robots driven by frameless fluid electrode dielectric elastomer actuators", "Science Robotics", Apr. 25, 2018, 8 pp., 3, eaat1893.
(Continued)

*Primary Examiner* — Edgardo San Martin
(74) *Attorney, Agent, or Firm* — Kaplan Breyer Schwarz, LLP

(57) ABSTRACT

Artificial muscles comprising a body of dielectric elastomer, wherein the body contains a pair of microfluidic networks are presented. Each microfluidic network includes a plurality of channels fluidically coupled via a manifold. The channels of the microfluidic networks are interdigitated and filled with conductive fluid such that each set of adjacent channels functions as the electrodes of an electroactive polymer (EAP) actuator. By using the manifolds as compliant wiring to energize the electrodes, artificial muscles in accordance with the present disclosure mitigate some or all of the reliability problems associated with prior-art artificial muscles.

13 Claims, 8 Drawing Sheets

Related U.S. Application Data

(60) Provisional application No. 62/745,599, filed on Oct. 15, 2018, provisional application No. 62/684,856, filed on Jun. 14, 2018.

(51) Int. Cl.

| | |
|---|---|
| *B33Y 80/00* | (2015.01) |
| *A61H 1/02* | (2006.01) |
| *F15B 21/06* | (2006.01) |
| *F03G 7/06* | (2006.01) |
| *A61F 2/70* | (2006.01) |
| *A61H 3/00* | (2006.01) |
| *B25J 9/10* | (2006.01) |
| *F15B 15/10* | (2006.01) |
| *F15B 13/044* | (2006.01) |
| *A61F 2/48* | (2006.01) |

(52) U.S. Cl.
CPC ............... *A61H 3/00* (2013.01); *B25J 9/10* (2013.01); *B25J 9/1075* (2013.01); *B33Y 80/00* (2014.12); *F15B 13/044* (2013.01); *F15B 15/103* (2013.01); *F15B 21/065* (2013.01); *H02N 1/004* (2013.01); *A61F 2/482* (2021.08); *A61F 2002/0894* (2013.01); *A61H 2201/1207* (2013.01); *F15B 2215/305* (2013.01)

(58) Field of Classification Search
CPC .... A61F 2/48; A61F 2/482; A61F 2002/0894; A61H 1/02; A61H 2201/1207; A61H 2201/12; B25J 9/10; B25J 9/1075; B33Y 80/00

See application file for complete search history.

(56) References Cited

U.S. PATENT DOCUMENTS

| | | | |
|---|---|---|---|
| 7,834,527 B2 | 11/2010 | Alvarez et al. | |
| 7,966,074 B2 | 6/2011 | Kim et al. | |
| 8,574,716 B2 | 11/2013 | Wu et al. | |
| 10,270,370 B2 | 4/2019 | Kim et al. | |
| 10,302,586 B2 | 5/2019 | Sun et al. | |
| 10,749,448 B2 | 8/2020 | Lindsay et al. | |
| 10,906,168 B2 | 2/2021 | Kornbluh et al. | |
| 10,910,960 B2 | 2/2021 | Shin et al. | |
| 10,995,779 B2 * | 5/2021 | Keplinger | H02N 1/006 |
| 11,060,511 B1 * | 7/2021 | Kartalov | A61F 2/70 |
| 2010/0133952 A1 | 6/2010 | Bang et al. | |
| 2018/0243110 A1 * | 8/2018 | Parra | H01L 41/0836 |
| 2018/0263839 A1 | 9/2018 | Lim et al. | |
| 2020/0032822 A1 | 1/2020 | Keplinger et al. | |
| 2020/0287478 A1 | 9/2020 | Kawabayashi | |
| 2021/0050800 A1 | 2/2021 | Jones et al. | |

OTHER PUBLICATIONS

Christoph Keplinger et al., "Stretchable, Transparent, Ionic Conductors," "Science", Aug. 30, 2013, DOI: 10.1126/science.1240228, pp. 984-987, vol. 341.

F. Carpi et al., "Artificial muscles based on dielectric elastomer actuators: Achievements and Challenges", Primo Congresso Nazionale di Bioingegneria (Congresso GNB2008), Pisa, 3-5 Iuglio 2008, Jan. 1, 2008, 3 pp.

F. Carpi et al., "Electroactive polymer artificial muscles: an overview", "Design and Nature V", "Wit Transactions on Ecology and the Environment", dated 2010, doi:10.2495/DN100311, ISSN 1743-3541 (on-line), pp. 353-364, vol. 138.

Huu Nguyen Chuc et al., "Fabrication and Control of Rectilinear Artificial Muscle Actuator," IEEE/ASME Transactions on Mechatronics, Feb. 1, 2011, DOI:10.1109/TMECH.2009.2038223, pp. 167-176, vol. 16, No. 1.

John A. Rogers, "A Clear Advance in Soft Actuators", "Science", Aug. 30, 2013, Publisher: American Association for the Advancement of Science, DOI: 10.1126/science.1243314, print ISSN 0036-8075; online ISSN 1095-9203, pp. 968-969, vol. 341 (6149).

John D. Madden et al., "Artificial Muscle Technology: Physical Principles and Naval Prospects", Paper # 17, Oct. 23, 2003, pp. 1-23.

Lauren R. Finkenauer et al., "Compliant liquid metal electrodes for dielectric elastomer actuators," Proceedings of SPIE, Event: SPIE Smart Structures and Materials + Nondestructive Evaluation and Health Monitoring, 2014, San Diego, California, United States, Mar. 8, 2014, doi: 10.1117/12.2049112, pp. 905631-1 to 905631-7, vol. 9056.

Notice of Allowance and Fees Due (PTOL-85) dated Mar. 23, 2021 for U.S. Appl. No. 16/442,092.

Rebecca K. Kramer et al., "Wearable Tactile Keypad with Stretchable Artificial Skin", May 9, 2011, Publisher: IEEE, Published in: 2011 IEEE International Conference on Robotics and Automation, Conference Location: Shanghai, China, DOI: 10.1109/ICRA.2011.5980082, 5 pp.

Requirement for Restriction/Election dated Sep. 21, 2020 for U.S. Appl. No. 16/442,092.

Samuel K. Sia et al., "Microlluidic devices fabricated in poly(dimethylsiloxane) for biological studies", "Electrophoresis", Jun. 19, 2003, Publisher: WILEY-VCH Verlag GmbH & Co. KGaA, DOI 10.1002/elps.200305584, pp. 3563-3576, 2003, 24.

\* cited by examiner

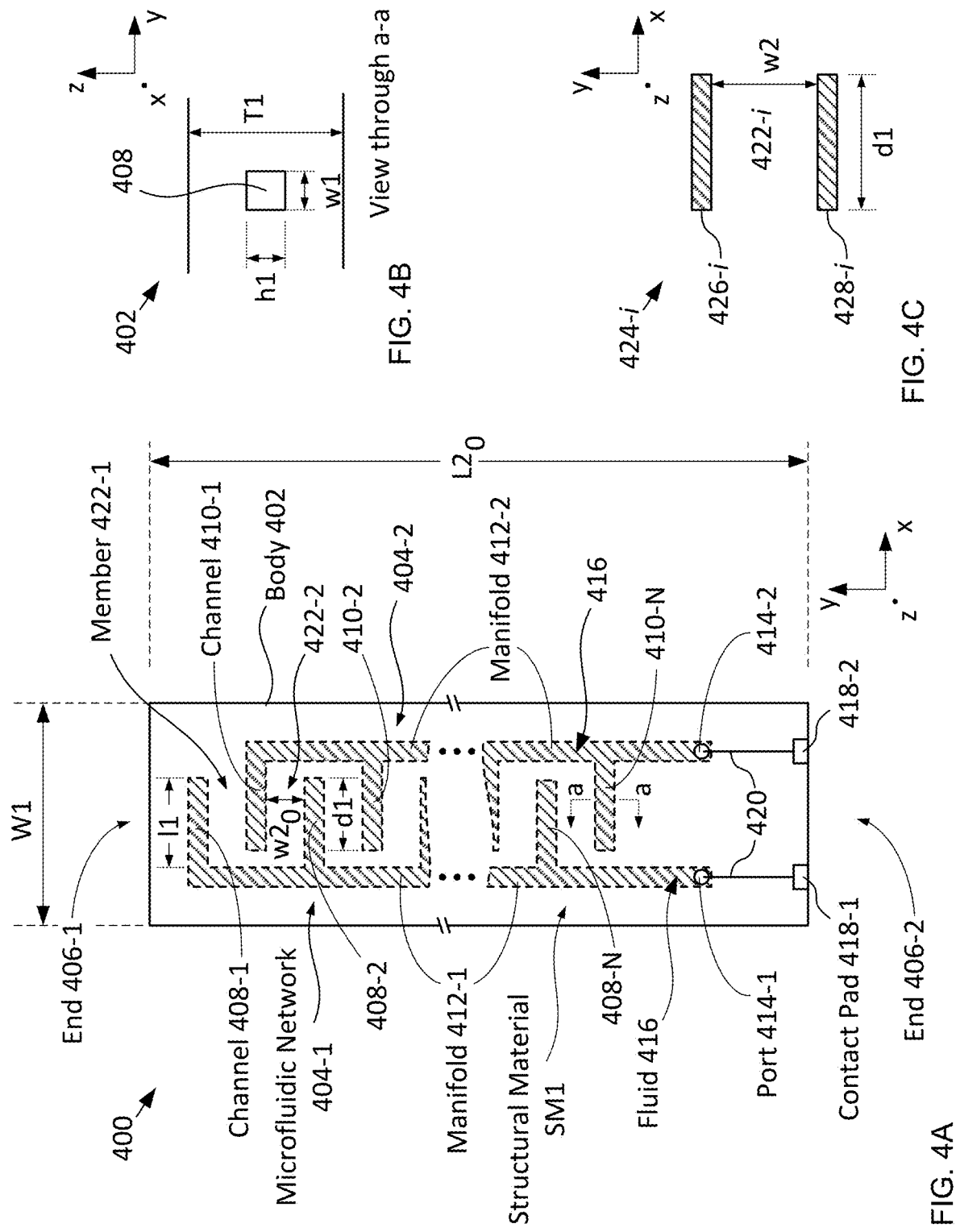

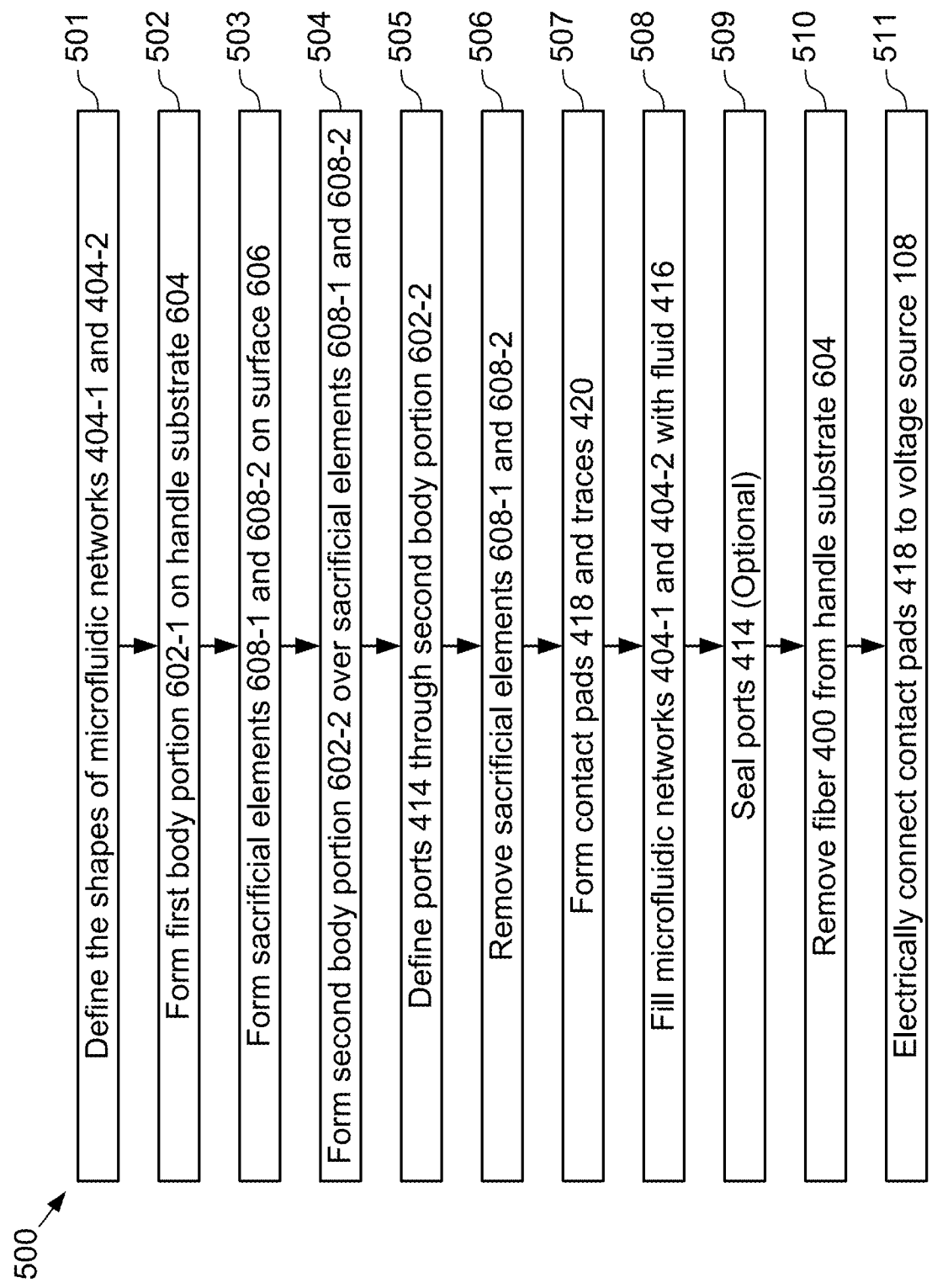

MICROFLUIDIC-BASED ARTIFICIAL MUSCLES AND METHOD OF FORMATION

CROSS REFERENCE TO RELATED APPLICATIONS

This application is a continuation of co-pending U.S. patent application Ser. No. 16/442,092, filed Jun. 14, 2019, entitled "Microfluidic-Based Artificial Muscles and Method of Formation", which claims the benefit of U.S. Provisional Application Ser. No. 62/684,856, filed Jun. 14, 2018, entitled "Biomimetic Force Generation By Soft Microfluidic Capacitor Stack" and U.S. Provisional Application Ser. No. 62/745,599, filed Oct. 15, 2018, entitled "Biomimetic Force Generation By Soft Microfluidic Capacitor Stack", each of which is incorporated herein by reference. If there are any contradictions or inconsistencies in language between this application and one or more of the cases that have been incorporated by reference that might affect the interpretation of the claims in this case, the claims in this case should be interpreted to be consistent with the language in this case.

TECHNICAL FIELD

The present disclosure relates to electrostatic actuators in general, and, more particularly, to electrostatic actuators suitable for use in exoskeletons, prosthetics, and vehicle propulsion.

BACKGROUND

Practical artificial muscles are sought after for use in a wide range of applications, including exoskeletons for augmenting human strength and capability, wearable electronic devices, prosthetic devices, walking robots, and acoustically quiet underwater propulsion systems.

Artificial muscles have been the subject of investigation for several years, with the strongest emphasis being on conventional technologies such as electromagnetics, pneumatics, hydraulics, thermal actuators, shape-memory alloys, and electrically active polymers (EAP). Unfortunately, as practiced in the prior art, these technologies have many drawbacks that make them impractical for use in many artificial-muscle applications.

Electromagnetic devices, such as linear and rotary electric motors, require high magnetic fields to generate significant force. The generation of high magnetic fields, however, requires large numbers of windings and/or high electric currents. As a result, electromagnetic devices tend to be large, bulky, and power hungry.

A pneumatic or hydraulic device can generate high force, but requires bulky and complex arrangements of tubing that are not suitable for many applications. Furthermore, the force-generation capability of such devices does not scale well into the small size domain required in most artificial muscles.

Thermal actuators can also generate significant force, but are slow and consumer a great deal of power. Furthermore, it can be difficult to remove heat effectively, once it has been generated to induce actuation. Since actuation speed and frequency are limited by heat-transfer rates, such actuators are not fast enough for artificial muscles in typical applications.

Shape-memory alloys (SMA) are metal alloys that can be easily deformed when below a "transition temperature" but return to the shape in which they were formed when heated above this temperature. While SMA artificial muscles have been demonstrated, the material is heavy, actuation tends to be slow, they consume considerable power, and the removal of heat to reverse actuation can be a challenge.

Electroactive polymers (EAP) actuators are elements that change shape under the influence of an applied electric field and are typically considered to most closely emulate biological muscles. Unfortunately, conventional approaches to fabricating EAP actuators are cumbersome, complicated, and not reproducible. Furthermore, many conventional EAP actuators have very poor efficiencies and are not durable. In addition, EAP actuators have historically proven difficult to manufacture.

The need for a simple, easily fabricated actuation technology suitable for use in artificial muscles remains, as yet, unmet in the prior art.

SUMMARY

The present disclosure is directed to artificial muscles based on arrays of electrostatic actuators that include resilient dielectric material disposed between liquid, semi-liquid, or gel electrodes. Artificial muscles in accordance with the present disclosure are particularly well suited for use in acoustically quiet propulsion systems for underwater vehicles, armored exoskeletons, and prosthetics.

Like artificial muscles known in the prior art, embodiments in accordance with the present disclosure employ electrostatic actuators that comprise a resilient dielectric material that is sandwiched between a pair of compliant electrodes. Unfortunately, prior-art electrostatic actuators, such as EAP actuators, are difficult to fabricate in high volume, complex, and unreliable due, in part, to the poor quality of the flexible electrodes used in them. Furthermore, these flexible electrodes require complicated interconnection schemes to actuate arrays of actuators.

In sharp contrast to the prior art, embodiments in accordance with the present disclosure employ a body of dielectric elastomer that contains a pair of microfluidic networks, each comprising a plurality of channels and a manifold that are filled with conductive fluid (e.g., a liquid, semi-liquid, gel, fluid suspension, etc.). The body and the channels collectively define one or more arrays of electrostatic actuators having a dielectric-elastomer member sandwiched between a set of opposing electrodes that are defined by the conductive-fluid-filled channels. The channels of each microfluidic network are electrically and fluidically coupled via its respective manifold. The use of such manifolds enables fluidically and electrically interconnection of large numbers of channel electrodes with high reliability.

An illustrative embodiment is an artificial muscle fiber comprising a serially connected array of micro-capacitors each having liquid positive and negative electrodes separated by an intervening dielectric material. The positive electrodes of the capacitors are electrically and fluidically coupled via a first manifold. The negative electrodes of the capacitors are electrically and fluidically coupled via a second manifold. In response to a voltage differential applied to the first and second manifolds, the electrodes of each capacitor generate an electrostatic force that induces a stress (Maxwell stress) on its intervening dielectric. The induced stress gives rise to a compressive force in each actuator and/or a compression of each capacitor, which manifests as a reduction in the total length of the muscle fiber and/or a "pull-in" force (i.e., tension) between the two ends of the muscle fiber.

In the illustrative embodiment, the artificial muscle fiber is formed via 3D printing of bulk structural material that comprises a resilient dielectric. Microfluidic channels that define each manifold and its associated channels are formed simultaneously. In some embodiments, a network of sacrificial material is first formed in the shapes of the manifolds and electrodes. The structural material is then 3D printed around the sacrificial material. Afterward, the sacrificial material is removed, thereby generating the microfluidic channels that define the manifolds and their associated channels. These channels are then filled with a liquid conductor via their manifolds using a conventional process, such as dead-end priming, etc.

In some embodiments, a sphincter-like artificial fiber is formed by arranging first and second arrays of electrodes radially about a center point of a disk of resilient dielectric such that each of the second array of electrodes is between a pair of electrodes of the first array. The electrodes of the first array are electrically and fluidically coupled via a first manifold and the electrodes of the second array are electrically and fluidically coupled via a second manifold. When a voltage differential is applied to the first and second manifolds, the first and second arrays of electrodes are attracted to one another giving rise to radial compression of the dielectric that manifests in the bulging of the disk.

In some embodiments, one- or two-dimensional arrangements of linear muscle fibers are defined to realize a muscle-fiber bundle capable of generating significant force.

An embodiment in accordance with the present disclosure is an artificial muscle comprising: a first body comprising a first material that is a dielectric elastomer; a first plurality of channels; a second plurality of channels, wherein the channels of the first plurality thereof and the channels of the second plurality thereof are interdigitated and spaced apart within the first body; a first manifold located within the first body, wherein the first manifold is fluidically coupled with each of the first plurality of channels; and a second manifold located within the first body, wherein the second manifold is fluidically coupled with each of the second plurality of channels; wherein each of the first manifold, the first plurality of channels, the second manifold, and the second plurality of channels is filled with a second material that is electrically conductive, and wherein the second material is selected from the group consisting of a liquid and a gel; and wherein the first and second plurality of channels are configured such that the application of a voltage differential between the second material in the first manifold and the second material in the second manifold generates a first attractive force between each set of adjacent first and second channel.

Another embodiment in accordance with the present disclosure is an artificial muscle comprising: a first microfluidic network comprising a first manifold and a first plurality of channels, the first microfluidic network being filled with a first material that is electrically conductive; a second microfluidic network comprising a second manifold and a second plurality of channels, the second microfluidic network being filled with a second material that is electrically conductive; a plurality of members comprising a third material that is a dielectric elastomer; wherein the first microfluidic network, the second microfluidic network, and the plurality of members are arranged such that (1) the channels of the first plurality thereof and the channels of the second plurality thereof are interdigitated and (2) each member of the plurality thereof is between a set of adjacent first and second channels; and wherein the first and second plurality of channels are configured such that the application of a voltage differential between the first material in the first microfluidic network and the second material in the second microfluidic network gives rise to a compressive force on each member of the plurality thereof.

Yet another embodiment in accordance with the present disclosure is a method for forming an artificial muscle, the method comprising: forming a body that comprises a first material that is a dielectric elastomer, wherein the body includes (1) a first microfluidic network that includes a first plurality of channels and a first manifold that is fluidically coupled with each channel of the first plurality thereof and (2) a second microfluidic network that includes a second plurality of channels and a second manifold that is fluidically coupled with each channel of the second plurality thereof, wherein the first microfluidic network and second microfluidic network are arranged such that the channels of the first plurality thereof and the channels of the second plurality thereof are interdigitated and spaced apart; filling the first microfluidic network with a second material that is electrically conductive, wherein the second material is selected from the group consisting of a liquid and a gel; and filling the second microfluidic network with the second material.

BRIEF DESCRIPTION OF THE DRAWINGS

FIG. 4A depicts a schematic drawing of a top view of an illustrative embodiment of an artificial muscle fiber in accordance with the present disclosure.

FIG. 4B depicts a schematic drawing of a sectional view of a representative channel 408 in accordance with the illustrative embodiment.

FIG. 4C depicts a schematic drawing of a sectional view of actuator 424-*i* in its nascent state.

FIG. 5 depicts operations of a first exemplary method suitable for use in fabricating an artificial muscle in accordance with the illustrative embodiment.

DETAILED DESCRIPTION

Figure 1:
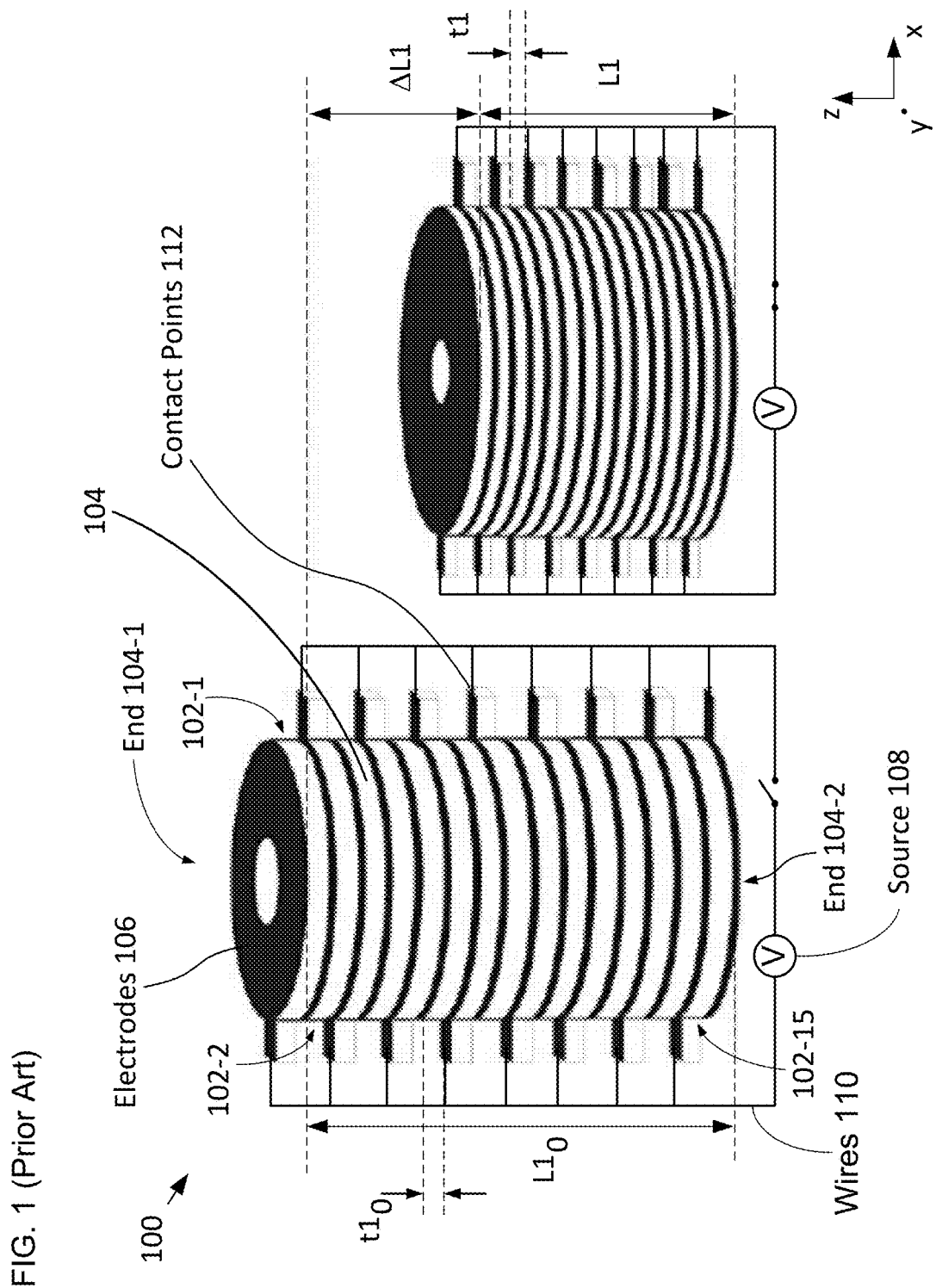
FIG. 1 depicts a schematic drawing of side views of a prior-art linear actuator proposed for use in an artificial muscle in its unactuated and actuated states.

FIG. 1 depicts a schematic drawing of side views of a prior-art linear actuator proposed for use in an artificial muscle in its unactuated and actuated states. Actuator 100 includes electroactive polymer (EAP) actuators 102-1 through 102-15, which are stacked in series to define a linear structure having ends 104-1 and 104-2. Actuator 100 is analogous to actuators disclosed by Chuc, et al., in "Fabrication and Control of Rectilinear Artificial Muscle Actuator," *IEEE/ASME Trans. on Mechatronics*," Vol. 16, pp. 167-176 (2011).

Each of EAP actuators 102-1 through 102-15 (referred to, collectively, as EAP actuators 102) includes layer 104 having an electrode 106 disposed on each of its top and bottom surfaces. Adjacent EAP actuators share a common electrode 106 at the interface between them. Each EAP actuator 102 has a nascent thickness, $t1_0$, in its unactuated state.

Layer 104 is typically a dielectric elastomer, such as acrylic elastomers, polydimethylsiloxane (PDMS), and the like.

To accommodate deformation of EAP actuator 102, each of electrodes 106 preferably comprises a compliant electrically conductive material or layer, such as carbon grease, saline solutions, liquid metals, microcracked metals, serpentine-shaped metal layers, carbon nanotubes (CNT), gel electrolytes, ionic hydrogels formed with salt water, graphene, ionic conductors (e.g., electrolytes, etc.), or surface-implanted layers of metallic nanoclusters.

Electrodes 106 are electrically connected to voltage source 108 by conventional wires 110, each of which is electrically connected to an electrode at a contact point 112.

In its unactuated state, actuator 100 has a total nascent length, $L1_0$, between ends 104-1 and 104-2, which is equal to N times the nascent thickness, $t1_0$, of each EAP actuator 102.

When voltage, V, is applied between the electrodes 106 through wires 110-1 and 110-2, an electrostatic force develops between the electrodes of each EAP actuator giving rise to a compression of its elastomer layer and a reduction of its thickness. As a result, each EAP actuator is compressed to a reduced thickness, t1, and the total length of actuator 100 is reduced to actuated length, L1. Ends 104-1 and 104-2 are drawn together by displacement, $\Delta L1$, which is equal to N times the compression induced in each EAP actuator 102.

It should be noted that, as actuator 100 shrinks in length, contact points 112 move closer together. As a result, shear stress can develop at these contact points, which can cause delamination of the electrode material, breakage of a wire, or another failure that results in an electrical disconnection of one or more wires from their respective contact points.

Figure 2:
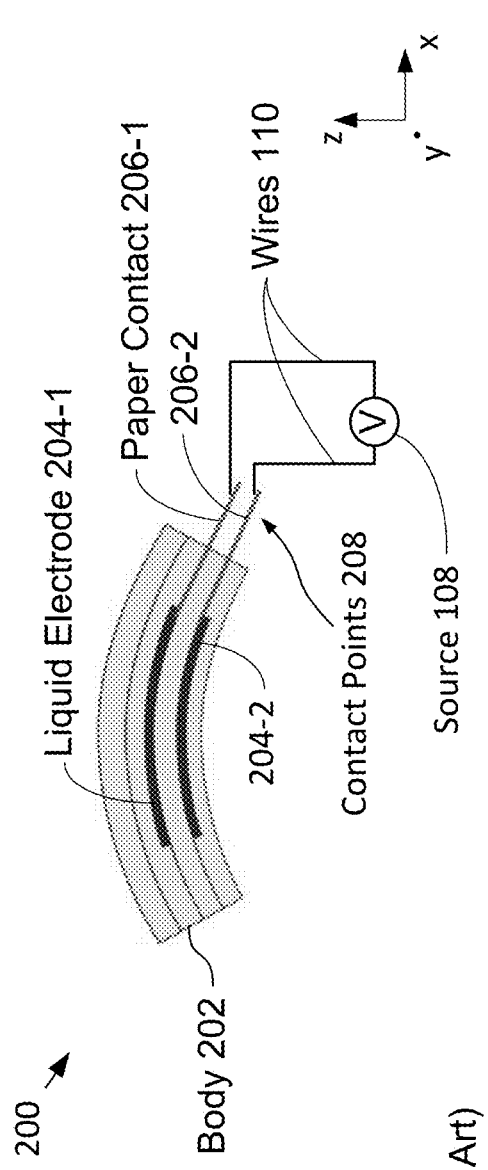
FIG. 2 depicts a schematic drawing of a cross-sectional view of another prior-art actuator proposed for use in an artificial muscle.

FIG. 2 depicts a schematic drawing of a cross-sectional view of another prior-art actuator proposed for use in an artificial muscle. Actuator 200 is a cantilever actuator whose curvature depends on the voltage applied across its electrodes. Actuator 200 comprises body 202, liquid electrodes 204-1 and 204-2, and paper contacts 206-1 and 206-2. Actuator 200 is analogous to actuators disclosed by Finkenauer, et al., in "Compliant liquid metal electrodes for dielectric elastomer actuators," *Proc. of SPIE*," Vol. 9056, pp. 905631-1 to 905631-7 (2014).

Body 202 is a cantilever structure comprising a dielectric elastomer, such as PDMS. Body 202 encloses liquid electrodes 204-1 and 204-2, each of which comprises a liquid metal alloy—specifically, eutectic Gallium-Indium.

Paper contacts 206-1 and 206-2 are provided to enable electrical contact to the liquid electrodes. Each paper contact is a partial sheet of conductive paper that is inserted into the structure by hand before the material of body 202 is fully cured.

Wires 110 are electrically connected to paper contacts 206-1 and 206-2 at contact points 208 to enable voltage source 108 to provide a voltage differential across the paper contacts.

As will be apparent to one skilled in the art, actuator 200 has several significant drawbacks that make it unattractive for use in practical artificial muscles. First, its assembly requires steps that must be performed by hand; therefore, it is not well suited to mass manufacture. Second, the use of paper contacts gives rise to serious reliability issues. Third, as discussed above with respect to actuator 100, motion of actuator 200 during actuation can cause shear stress at contact points 208 that can lead to device failure.

Figure 3:
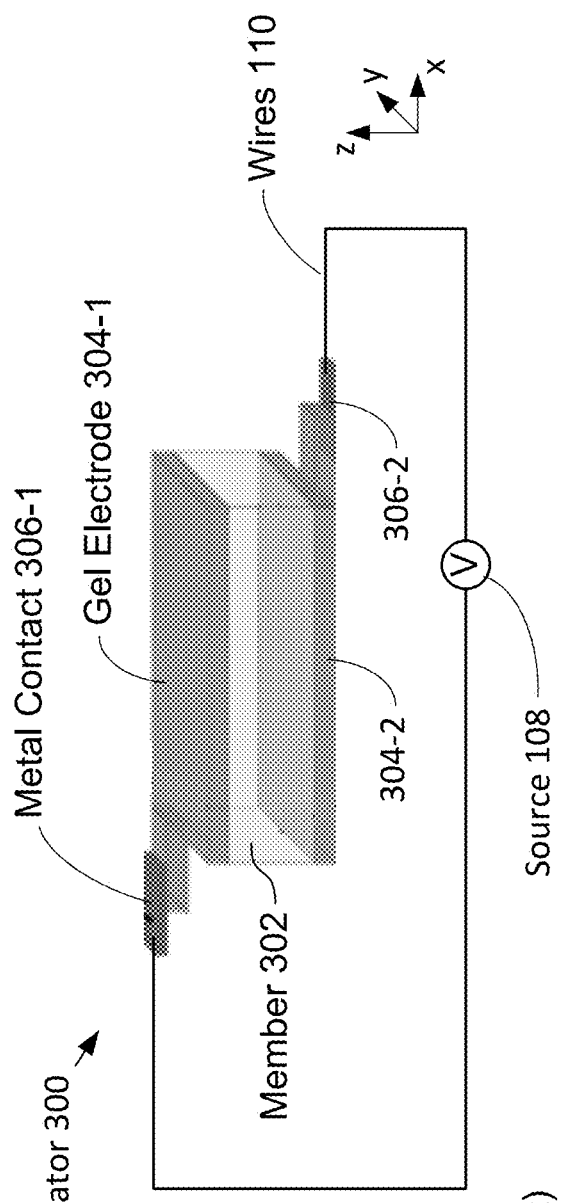
FIG. 3 depicts a schematic drawing of a cross-sectional view of yet another prior-art actuator proposed for use in an artificial muscle.

FIG. 3 depicts a schematic drawing of a cross-sectional view of yet another prior-art actuator proposed for use in an artificial muscle. Actuator 300 is an EAP actuator whose thickness, t2, depends on the voltage applied across its electrodes. Actuator 300 comprises member 302, gel electrodes 304-1 and 304-2, and contacts 306-1 and 306-2. Actuator 300 is analogous to actuators disclosed by Keplinger, et al., in Stretchable Transparent Ionic Conductors," *Science, Vol.* 341, pp. 984-987 (2013).

Member 302 is a slab of dielectric elastomer, such as PDMS. The top and bottom surfaces of member 302 are coated with an electrolytic elastomer (e.g., polyacrylamide hydrogel containing sodium chloride).

Metal contacts 306-1 and 306-2 are copper sheets that are placed on their respective gel electrodes. Wires 110 are joined with the metal contacts at contact points 112, as discussed above, to electrically connect each of the metal contacts to voltage source 108.

Unfortunately, actuator 300 has all of the same drawbacks as those discussed above with respect to actuators 100 and 200. Furthermore, the electrolytic nature of gel electrodes 304-1 and 304-2 add an additional layer of complexity to the operation of actuator 300. Specifically, the interface between the metal contacts and the electrolyte material can form a double layer under certain bias conditions, which results in the double layer functioning as an additional capacitor.

It is an aspect of the present disclosure that at least some of the problems of prior art artificial muscles comprising pluralities of electrostatic actuators, such as EAP actuators, can be mitigated by employing microfluidic networks in the body of an artificial muscle, where the microfluidic networks are filled with an electrically conductive fluid. Furthermore, each microfluidic network includes a port at which a robust electrical connection to its conductive fluid can be made. For the purposes of this Specification, including the appended claims, the term "fluid" is defined as a liquid, semi-liquid, fluid suspension, gel, or equivalent.

FIG. 4A depicts a schematic drawing of a top view of an illustrative embodiment of an artificial muscle fiber in accordance with the present disclosure. Fiber 400 includes body 402, within which microfluidic networks 404-1 and 404-2 reside.

Body 402 is a substantially straight strip of structural material SM1. In the depicted example, structural material SM1 is a dielectric-elastomer—specifically, PDMS. Body 402 has width W1 and thickness T1 and extends from first end 406-1 to second end 406-2 to define nascent length $L2_0$. In the depicted example, body comprises PDMS, L2=20 cm, W1=10 mm, and T1=100 microns; however, in some embodiments, body 402 comprises a different suitable dielectric elastomer and/or has a different width and/or thickness. Furthermore, although fiber 400 is depicted as being straight, it should be noted that fiber 400 can have any practical shape (e.g., curved in one or more dimensions, helical, etc.) without departing from the scope of the present disclosure.

Fluidic network 404-1 includes channels 408-1 through 408-N (where N is any practical number), manifold 412-1, and port 414-1.

Fluidic network 404-2 includes channels 410-1 through 410-N (referred to, collectively, as channels 410), manifold 412-2, and port 414-2.

FIG. 4B depicts a schematic drawing of a sectional view of a representative channel 408 within body 402 in accordance with the illustrative embodiment. The sectional view shown in FIG. 4B is taken through line a-a shown in FIG. 4A and the depicted channel is representative of each of channels 408-1 through 408-N (referred to, collectively, as channels 408) and 410-1 through 410-N (referred to, collectively, as channels 410).

Each of channels 408 and 410 is a microchannel that resides completely within body 402. channels 408 and 410 are substantially identical and have length l1, width w1, and height h1. In the depicted example, channels 408 and 410 are approximately 6 mm long (i.e., l1=6 mm) and have a substantially square cross-section and w1 and h1 are each approximately 30 microns. channels 408 and 410 are interdigitated to define overlap distance, d1. In the depicted example, d1 is equal to approximately 5.3 mm.

Returning now to FIG. 4A, each of manifolds 412-1 and 412-2 (referred to, collectively, as manifolds 412) is a microfluidic channel that resides within body 402. In the depicted example, each of manifolds 412 has the same cross-sectional dimensions as channels 408 and 410; however, one or more of the manifolds and channels can have different dimensions without departing from the scope of the present disclosure.

Ports 414-1 and 414-2 (referred to, collectively, as ports 414) are openings through body 402 that enable microfluidic networks 404-1 and 404-2, respectively, to be filled with conductive fluid. In some embodiments, each of ports 414 is located at a position in body 402 that does not undergo significant motion during the actuation of fiber 400 to mitigate the potential for electrical failure.

Manifold 412-1 extends from channel 408-1 to port 414-1, thereby fluidically coupling port 414-1 with each of channels 408.

In similar fashion, manifold 412-1 extends from channel 410-1 to port 414-2, thereby fluidically coupling port 414-2 with each of channels 410.

Each of microfluidic networks 404-1 and 404-2 is filled with fluid 416, which is a conventional electrically conductive fluid. In the depicted example, fluid 416 is saline; however, myriad conductive liquids and/or gels can be used in one or both microfluidic networks without departing from the scope of the present disclosure. Conductive fluids suitable for use in accordance with the present disclosure include, without limitation, carbon grease, saline solutions, liquid metals, liquid electrolytes, gel electrolytes, ionic hydrogels formed with salt water, ionic conductors, and the like.

Typically, microfluidic networks 404-1 and 404-2 are filled with the same conductive fluid; however, in some embodiments, the microfluidic networks are filled with different conductive fluids.

Contact pads 418-1 and 418-2 (referred to, collectively, as contact pads 418) are conventional metal contacts disposed on the outer surface of body 402. Each of contact pads 418 is electrically connected to its respective port 414 via a conventional electrical trace 420. When microfluidic networks 404-1 and 404-2 are filled with fluid 416, therefore, contact pads 418 are in electrical contact with the conductive fluid, thereby enabling robust electrical connectivity between the microfluidic networks and voltage supply 108 (not shown).

Members 422-1 through 422-N (referred to, collectively, as members 422) are portions of body 402 having nascent width w2$_0$. Each of members 422 resides between a different set of adjacent interdigitated channels 408 and 410. For example, member 422-1 lies between channels 408-1 and 410-1, member 422-2 lies between channels 408-2 and 410-2, and so on. In the depicted example, nascent width w2$_0$ is equal to 10 microns; however, any suitable nascent width can be used for members 422 without departing from the scope of the present disclosure.

As will be appreciated by one skilled in the art, when channels 408-$i$ and 410-$i$, where $i$=1 through N, are filled with fluid 416, they function as electrodes that oppose each other across their respective member 422-$i$, thereby collectively defining parallel-plate capacitor-based electrostatic actuator 424-$i$.

FIG. 4C depicts a schematic drawing of a sectional view of electrostatic actuator 424-$i$ in its nascent state. The sectional view shown in FIG. 4C is taken through the middle of the thickness of the electrostatic actuator. Electrostatic actuator 424-$i$ includes electrodes 426-$i$ and 428-$i$, which are defined by fluid-filled channels 408-$i$ and 410-$i$, respectively.

When each of actuated by applying a voltage between ports 414-1 and 414-2, the compressive force applied to member 422-$i$ is given by:

$$F = \frac{A\varepsilon_0 \varepsilon_r^2 V^2}{2 \cdot w2^2}, \quad (1)$$

where V is the applied voltage, A is the area of the opposing faces of electrodes 426-$i$ and 428-$i$ (i.e., h1×d1), w2 is the separation between these faces, and $\varepsilon_r$ is the relative dielectric constant of structural material SM1.

Expressed in terms of force per unit cross-sectional area of the electrodes, equation (1) becomes:

$$F = \frac{\varepsilon_0 \varepsilon_r^2 V^2}{2 \cdot w2^2}. \quad (2)$$

For the dimensions of fiber 400 provided above, and using a value of 2.5 for the relative dielectric constant of PDMS, for an applied voltage of 3 kV, the generated force per unit area for electrostatic actuator 424-$i$ is approximately 249 N/cm$^2$ (i.e., 362 lbs./in$^2$).

Electrostatic actuators 424-1 through 424-N are stacked in series such that the compressive force generated at each of the actuators gives rise to "pull-in" force (i.e., a tension) between ends 406-1 and 406-2. Since electrostatic actuators 424-1 through 424-N are connected in series, however, they function as springs attached in series; thus, the compressive forces they generate are not cumulative. As a result, the tension generated between ends 406-1 and 406-2 is substantially equal to the force generated by a single electrostatic actuator. In some embodiments, the tension generated between ends 406-1 and 406-2 results in a reduction in the length of fiber 400.

It should be noted, however, that the contractions that occur at each electrostatic actuator are cumulative and can give rise to a macroscopic length change that is equal to N times the contraction of a single electrostatic actuator (assuming all actuators contract the same amount). In the depicted example, nascent length L2$o$ is approximately 20 cm, which enables approximately 2 cm of total contraction of fiber 400—approximately the amount a human bicep can contract.

As discussed below in more detail, an artificial muscle capable of generating more force can be formed by using a plurality of fibers 400 that are mechanically coupled in parallel.

While fiber 400 is, in some ways, analogous to actuator 100 described above, the use of microfluidic techniques in embodiments in accordance with the present disclosure provides significant advantages to that make practical artificial muscle fibers feasible. These advantages include:

i. conductive-fluid-filled channels are highly reliable compliant electrodes that function as compliant electrodes for electrostatic actuators; or
ii. conductive-fluid-filled manifolds that can flex and bend without the danger of wires snapping and disconnecting enables them to function as flexible and robust electrical wiring for electrically connecting the capacitor electrodes to a voltage source; or
iii. the formation of the microfluidic networks within the body of a muscle fiber eliminates the need for separate dielectric material and hard electrodes to be built into the muscle fiber; or
iv. formation of the microfluidic networks within the body of a muscle fiber enables high-volume manufacture because it can be easily automated by using, for example, three-dimensional (3D) printing, photolithographic-based patterned molding, MEMS fabrication techniques, silk-screening, etc.; or
v. any combination of i, ii, iii, and iv.

It should be further noted that muscles and/or muscle fibers in accordance with the present disclosure can be made such that they are monolithic using, for example, 3D-printed bulk dielectric and channels for soft wiring. Such monolithic structures are significantly sturdier and more robust than prior-art devices that comprise heterogeneous stacks of dissimilar materials (e.g., metals, polymers, paper electrodes, etc.). As a result, muscles and/or muscle fibers in accordance with the present disclosure can deliver and tolerate higher stresses before failure and can provide greater force safely and reliably.

FIG. 5 depicts operations of a first exemplary method suitable for use in fabricating an artificial muscle in accordance with the illustrative embodiment. Method 500 is described herein with continuing reference to FIGS. 4A-C, as well as reference to FIGS. 6A-C.

Figures 6A, 6B, 6C:
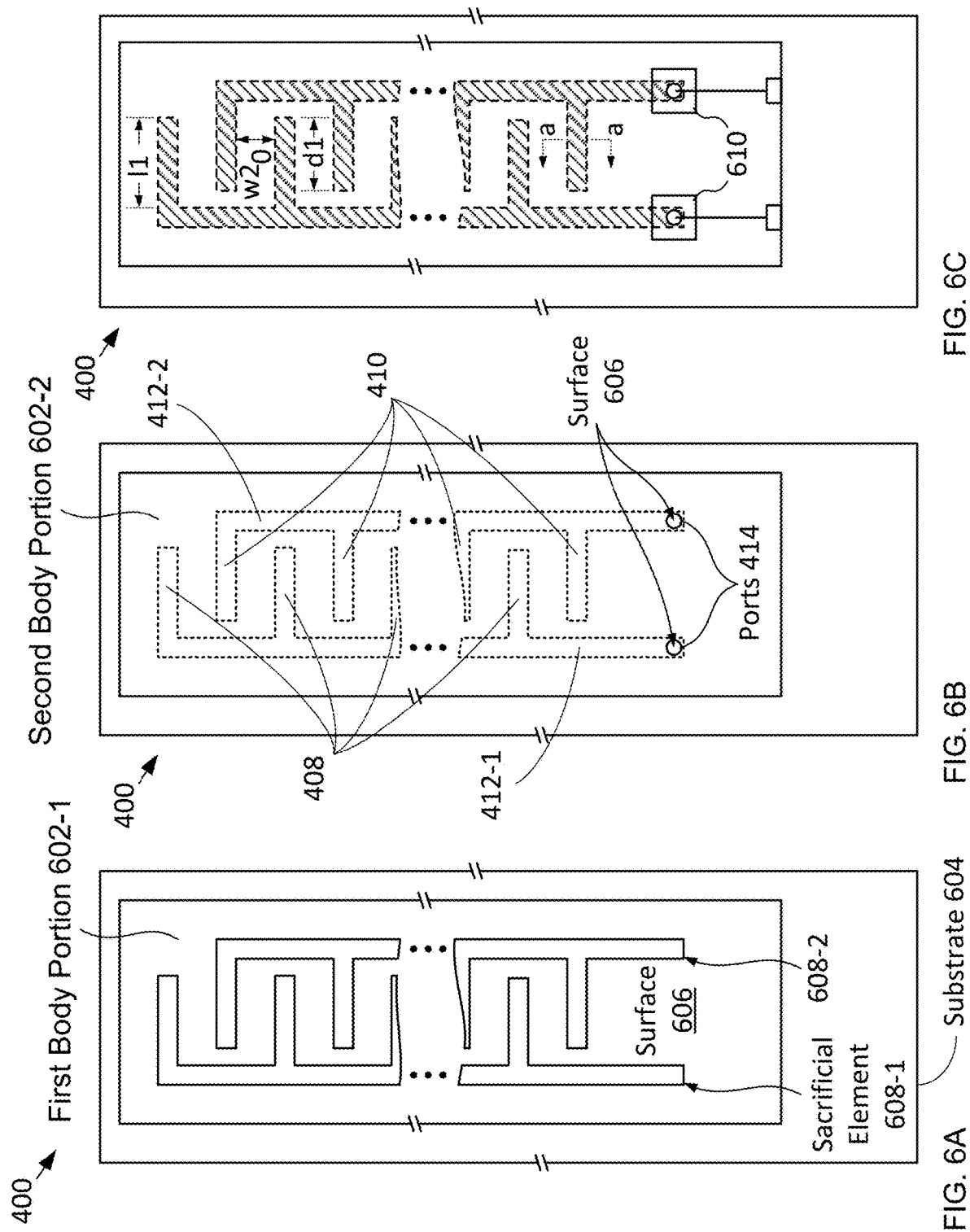
FIGS. 6A-C depict schematic drawings of top views of fiber 400 at different stages of its fabrication.

FIGS. 6A-C depict schematic drawings of top views of fiber 400 at different stages of its fabrication.

Method 500 begins with operation 501, wherein the shapes of microfluidic networks 404-1 and 404-2 are defined.

At operation 502, first body portion 602-1 is formed on handle substrate 604. Handle substrate 604 is a conventional substrate suitable for use in planar-processing fabrication.

First body portion 602-1 is a slab of structural material SM1 that is formed in conventional fashion. First body portion 602-1 includes top surface 606 and has a thickness of approximately 35 microns and lateral dimensions based on the desired size of fiber 400.

At operation 503, sacrificial elements 608-1 and 608-2 are formed on surface 606 of first body portion 602-1. In the depicted example, sacrificial elements 608-1 and 608-2 are photoresist patterns defined in the shapes of microfluidic networks 404-1 and 404-2, respectively, using conventional photolithography.

FIG. 6A shows nascent fiber 400 after the definition of sacrificial elements 608-1 and 608-2.

At operation 504, second body portion 602-2 is formed of structural material SM1 such that it encapsulates sacrificial elements 608-1 and 608-2. Second body portion 602-2 is formed such that it is a substantially conformal layer over the sacrificial elements and has a substantially planar top surface. The thickness of second body portion 602-2 is approximately 65 microns (outside of the regions of the sacrificial elements). The first and second body portions collectively define body 402 having a total thickness, therefore, of approximately 100 microns.

At operation 505, ports 414 are defined such that they extend through second body portion 602-2 and expose portions of sacrificial elements 608-1 and 608-2.

At operation 506, sacrificial elements 608-1 and 608-2 are removed in conventional fashion, thus defining empty manifolds 412-1 and 412-2 and channels 408 and 410.

FIG. 6B shows nascent fiber 400 after the removal of sacrificial elements 608-1 and 608-2.

At operation 507, contact pads 418-1 and 418-2 and conductive traces 420 are formed in conventional fashion. In some embodiments, traces 420 are defined such that they extend into ports 414 and onto surface 606 in each of manifolds 412-1 and 412-2.

At operation 508, microfluidic networks 404-1 and 404-2 are filled with fluid 416 using a conventional technique, such as dead-end priming under static pressure through ports 414, and the like.

At optional operation 509, seals 610 are bonded over ports 414 to mitigate leakage of fluid 416 out of the microfluidic networks. In the depicted example, seals 610 are regions of structural material SM1 that are formed separately and placed over the ports. In some embodiments, seals 610 are formed in a different conventional manner.

FIG. 6C shows nascent fiber 400 after seals 610 have been bonded over ports 414.

At operation 510, fiber 400 is removed from handle substrate 604.

At operation 511, wires 110 are attached to contact pads 418 to connect fiber 400 to voltage source 108.

It should be noted that method 500 represents merely one fabrication method suitable for use to form artificial muscles and/or muscle fibers in accordance with the present disclosure.

Another exemplary fabrication method suitable for use to fabricate muscles and/or muscle fibers disclosed herein is 3D printing via stereolithography (SLA), which requires no sacrificial material. In a representative SLA process, nascent body 402 is first formed from a liquid-monomer starting material. The monomer material in the structural regions of body 402 are the selectively polymerized using a directional laser beam to convert the monomer into structural material SM1, during which, the structure of the microfluidic networks is left as monomer material. After this polymerization step, the monomer material is removed by solvent, etc. to realize a device of only structural material SM1 that includes empty microfluidic networks 404-1 and 404-2. Microfluidic networks 404-1 and 404-2 are then filled with conductive fluid 416.

Yet another exemplary fabrication method suitable for use to fabricate muscles and/or muscle fibers disclosed herein is replication molding, in which the final shape of body 402 is separated into multiple layers, each of which can be formed via casting structural material SM1 into a mold designed for that layer. Each layer is then separated from its mold and the layers are assembled to realize the completed structure of body 402.

In some embodiments, body 402 and the conductive-fluid-filled microfluidic networks are formed by bulk-printing operations. Such approaches offer the advantage that no sacrificial material must be formed and subsequently removed; therefore, these methods are potentially faster and more efficient. Furthermore, their use offers the potential for simpler designs.

Figure 7:
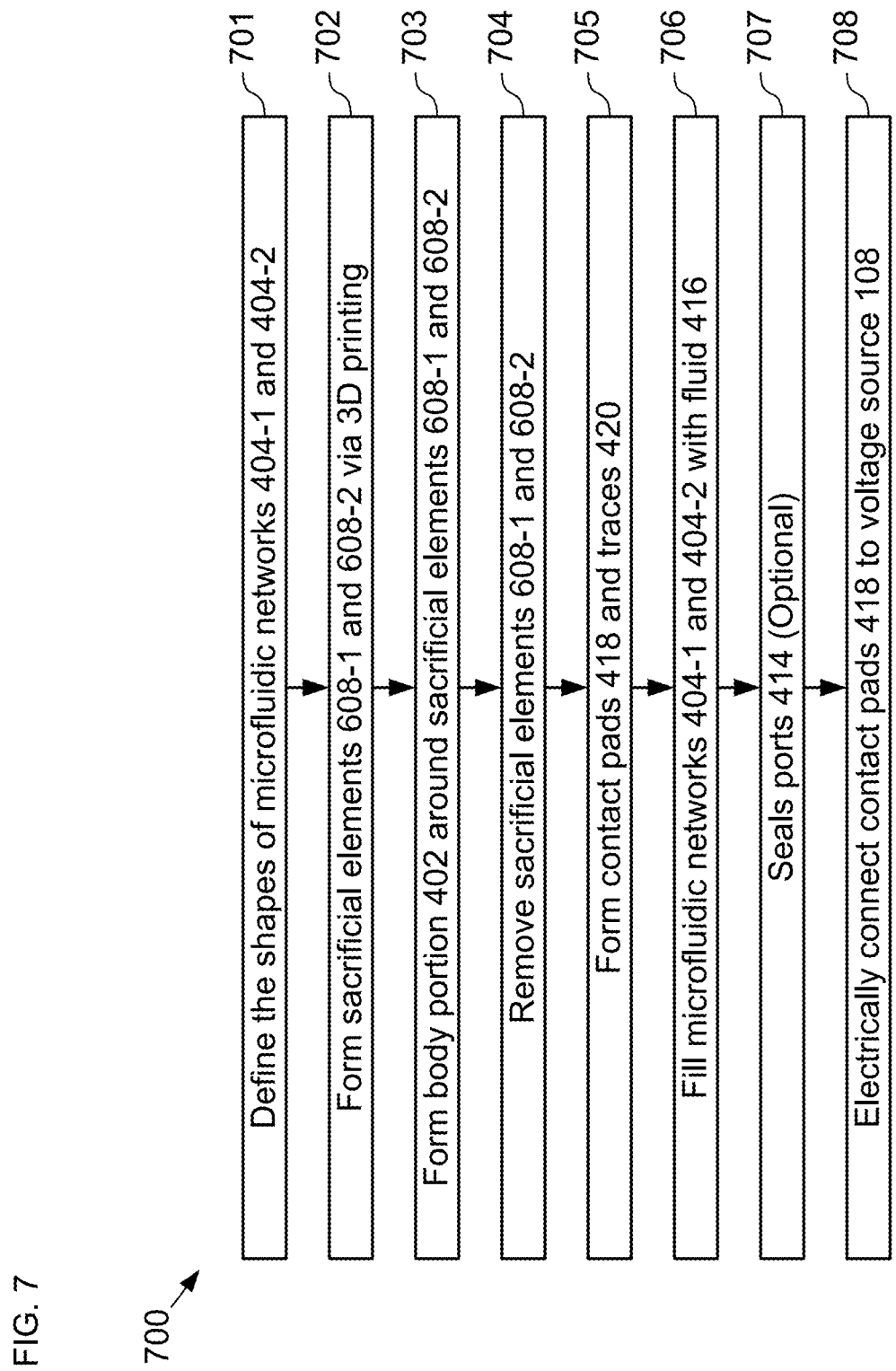
FIG. 7 depicts operations of a second exemplary method suitable for use in fabricating an artificial muscle in accordance with the illustrative embodiment.

FIG. 7 depicts operations of a second exemplary method suitable for use in fabricating an artificial muscle in accordance with the illustrative embodiment. Like method 500, method 700 begins with operation 701, wherein the shapes of microfluidic networks 404-1 and 404-2 are defined.

At operation 702, sacrificial elements 608-1 and 608-2 are formed in the shapes of microfluidic networks 404-1 and 404-2, respectively, via 3D printing. Sacrificial elements 608-1 and 608-2 are formed such that they comprise a material that can be removed (etched, melted, etc.) without significant damage to the structural material of body 402. It should be noted that, when using 3D printing to define the sacrificial elements, no handle substrate is necessary (although one can be used without departing from the scope of the present disclosure).

At operation 703, body 402 is formed around sacrificial elements 608-1 and 608-2 via 3D printing of structural material SM1. As noted above, in the depicted example, structural material SM1 is PDMS.

During operation 703, body 402 is formed such that ports 414 are defined during the printing process and a portion of each of sacrificial elements 608-1 and 608-2 is exposed.

In some embodiments, the structure of microfluidic networks 404-1 and 404-2 is written directly into body 402 as it is formed via 3D printing. In such embodiments, operation 702 is not included in method 700.

Furthermore, in some embodiments, operation 702 forms microfluidic networks 404-1 and 404-2, which are written directly into body 402 using an electrically conductive material (e.g., a polymer, etc.) that is flexible enough to function as compliant electrodes in electrostatic actuators 424. In such embodiments, no sacrificial material is needed and the entire muscle fiber can be completed in a single 3D printing process. This can be accomplished using, for example, stereolithography (SLA) 3D printing, as discussed above. At operation 704, sacrificial elements 608-1 and 608-2 are removed through ports 414 in conventional fashion.

At operation 705, contact pads 418-1 and 418-2 and traces 420 are formed.

At operation 706, microfluidic networks 404-1 and 404-2 are filled with fluid 416, as described above.

At optional operation 707, ports 414 are sealed to mitigate leakage of fluid 416 out of the microfluidic networks.

At operation 708, method 700 is completed with the attachment of wires 110 to contact pads 418 to connect fiber 400 to voltage source 108.

Although the methods presented herein are described with reference to fiber 400, it should be noted that any method in accordance with the present disclosure can be used to fabricate any artificial muscle or artificial muscle fiber in accordance with the present disclosure.

As noted briefly above, increasing the number of electrostatic actuators 424 connected in series increases the amount of contraction a muscle fiber can realize but does not increase the amount of force it can generate. In the depicted example, each of electrostatic actuators 424 can generate approximately 249 N/cm$^2$. The capacitive plate area of each electrostatic actuators 424 is only about $1.8\times10^{-3}$ cm$^2$, however, so each actuator can generate approximately 0.44 N of force. In order to generate an appreciable amount of force, a plurality of fibers 400 can be connected in parallel so that the forces they generate combine, as discussed below and with respect to FIG. 8.

Figure 8:
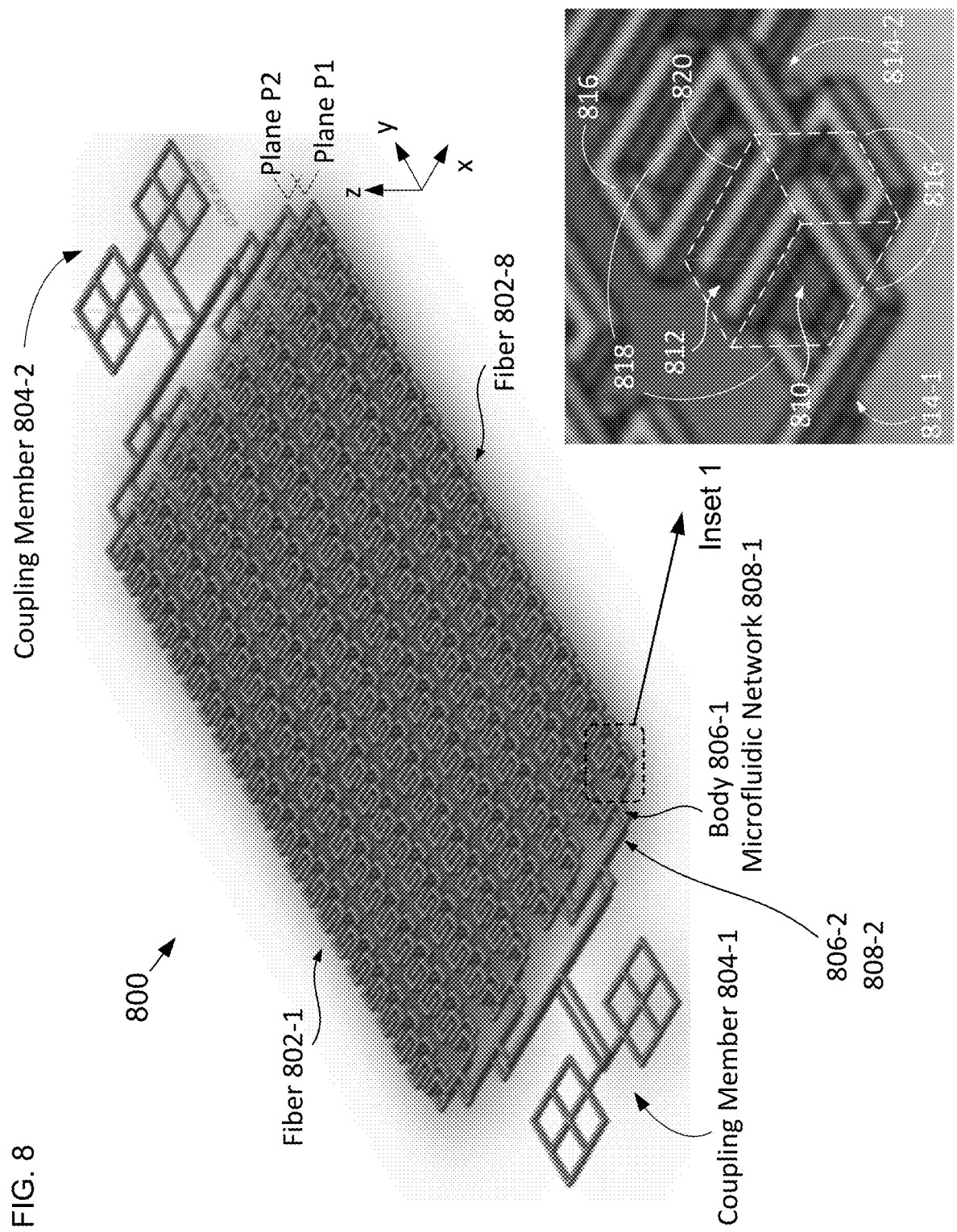
FIG. 8 depicts a schematic drawing of a perspective view of an artificial muscle fiber bundle in accordance with the present disclosure.

FIG. 8 depicts a schematic drawing of a perspective view of an artificial muscle fiber bundle in accordance with the present disclosure. Bundle 800 includes fibers 802-1 through 802-8 and coupling members 804-1 and 804-2.

Fibers 802-1 through 802-8 (referred to, collectively, as fibers 802), are analogous to fiber 400 described above; however, the bodies of each of fibers 802 are configured such that they follow the paths of their respective microfluidic networks. Fibers 802 are linearly arrayed along the x-direction, as indicated in FIG. 8.

Each fiber 802 consists of two entwining but non-crossing bodies 806-1 and 806-2 that encase microfluidic networks 808-1 and 808-2, respectively. In similar fashion to the microfluidic networks of fiber 400, microfluidic network 808-1 includes a plurality of channels 810, which are fluidically and electrically connected via manifold 814-1. Microfluidic network 808-2 includes a plurality of channels 812, which are fluidically and electrically connected via manifold 814-2.

As shown in Inset 1, bodies 806-1 and 806-2 and microfluidic networks 808-1 and 808-2 serpentine within each of planes P1 and P2 and periodically transition between the planes via an orthogonal member. As a result, manifold 814-1 has multiple manifold segments 816 in each plane and manifold 814-2 has multiple manifold segments 818 in each plane. Channels 810, located within the orthogonal members of body 806-1, run between planes P1 and P2 to fluidically couple manifold segments 816. In similar fashion, channels 812, located within the orthogonal members of body 806-2, run between planes P1 and P2 to fluidically couple manifold segments 818. When filled with conductive fluid, channels 810 and 812 form the opposing electrodes of electrostatic actuators 820.

As will be apparent to one skilled in the art, after reading this Specification, fabrication of the three-dimensional structure of fibers 802 via sacrificial molding requires a slight modification to method 500 described above.

For example, after the formation of first body portion 602-1, a first layer of sacrificial material is deposited on the top surface of the first body portion and defined in the shape of the manifold segments 816 and 818 that are located in plane P1. An intermediate body portion is then formed over the first body portion and the first layer of sacrificial material, where the intermediate body portion has a top surface that defines plane P2. Vias are then formed through the intermediate body portion to expose portions of the manifold segments in plane P1 and the vias are filled with sacrificial material to define the shapes of channels 810 and 812. A second layer of sacrificial material is then defined the top surfaces of the intermediate body portion and sacrificial-material-filled vias to form the shapes of the manifold segments 816 and 818 that are located in plane P2. A top body portion is then formed over the intermediate body portion and second layer of sacrificial material to complete body 802. Once body 802 is complete, method 500 can continue as described above with the removal of the sacrificial material, formation of ports and interconnect traces, the filling of the microfluidic networks with conductive fluid, and so on.

It should be noted that bundle 800 can be fabricated using any suitable fabrication process, including those discussed above (e.g., direct 3D printing with or without sacrificial material, replication molding, silk-screening, etc.).

Fluidic networks 808-1 of fibers 802 are fluidically and electrically connected at common ports (not shown) formed at each of coupling members 804-1 and 804-2. In similar fashion, microfluidic networks 808-2 of fibers 802 are also fluidically and electrically connected at different common ports formed at each of coupling members 804-1 and 804-2. As a result, bundle 800 has only one pathway for filling all of microfluidic networks 808-1 and one separate pathway for filling all of microfluidic networks 808-2. In addition, this enables the entire bundle to be electrically connected to voltage source 108 (not shown) via only two connection points. Still further, bundle 800 is configured in a binary fluidic architecture such that fluidic bias is mitigated and the electric and fluidic resistance is substantially equal among fibers 800.

It should be noted that the parallel fiber arrangement of bundle 800 is analogous to a parallel arrangement of M identical springs, which will produce M times the force generated by each spring for the same shared elongation. As a result, bundle 800 generates 8 times the force produced by each fiber 802.

In accordance with the present disclosure, therefore, an increase in the absolute elongation of bundle 800 can be realized by increasing the number of electrostatic actuators 816 along the length of each of its muscle fibers 802, while the force generated by bundle 800 can be increased by adding additional muscle fibers 802 and connecting all of the muscle fibers in parallel. Furthermore, additional bundles 800 can be arrayed along both x-axis and z-axis to gain even greater force.

Although bundle 800 includes fibers 802 that are arrayed in only the x-dimension, in some embodiments, fibers 802 are also arrayed in the z-direction to realize a two-dimensional bundle of muscle fibers and greater force-generation capability.

Figure 9:
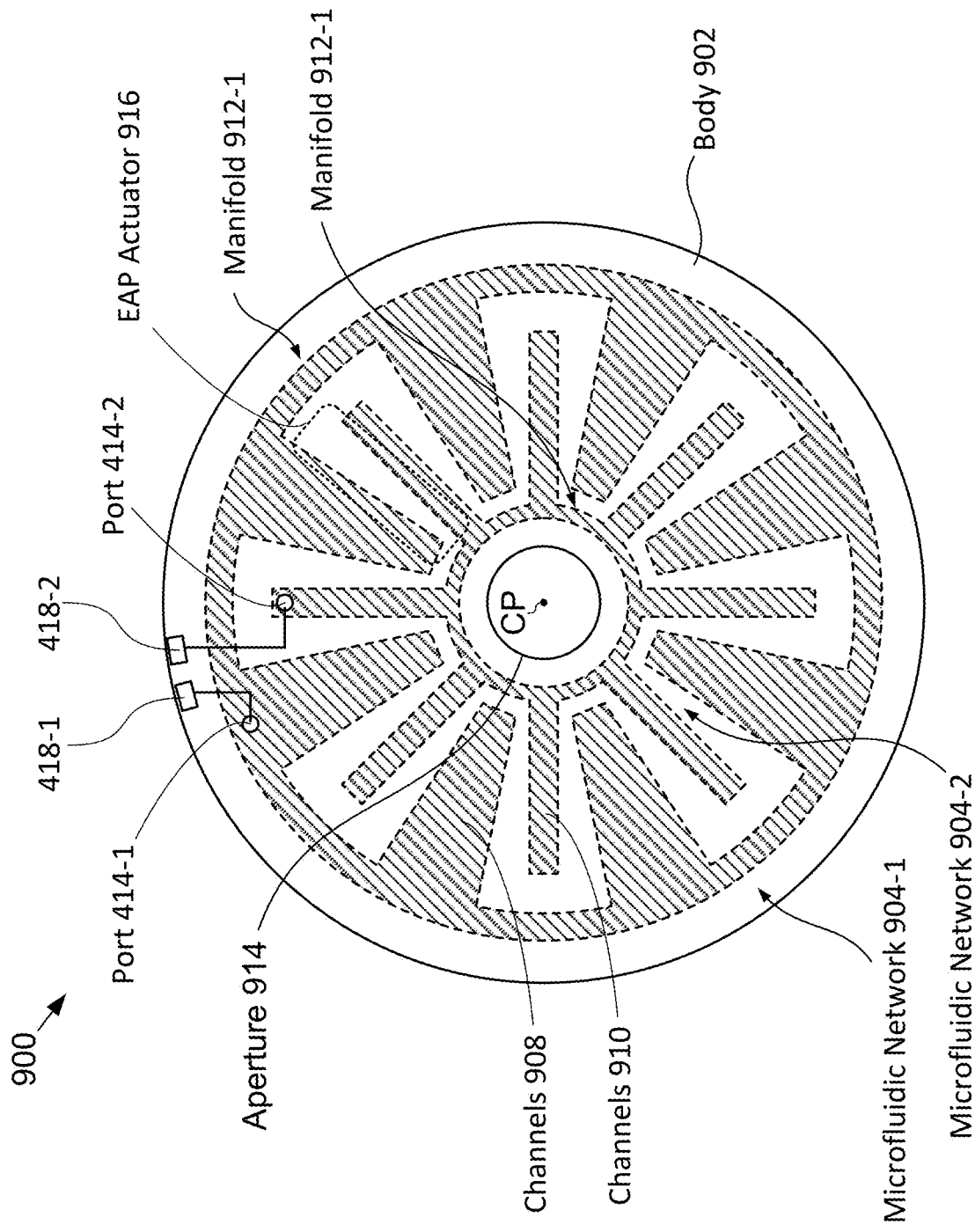
FIG. 9 depicts a schematic drawing of a top view of another artificial muscle in accordance with the present disclosure.

FIG. 9 depicts a schematic drawing of a top view of another artificial muscle in accordance with the present disclosure. Muscle 900 is an artificial sphincter that includes body 902, within which microfluidic networks 904-1 and 904-2 reside.

Body 902 is a substantially circular plate of dielectric-elastomer-based structural material. Body 902 is analogous to body 402 described above.

Fluidic network 904-1 includes channels 908-1 through 908-8, (referred to, collectively, as channels 908), manifold 912-1, and port 414-1.

Fluidic network 904-2 includes channels 910-1 through 910-8 (referred to, collectively, as channels 910), manifold 912-2, and port 414-2.

Channels 908 are uniformly spaced and arranged in a radial pattern about center point CP. Channels 908 are fluidically coupled with port 414-1 via manifold 912-1.

In similar fashion channels 910 are also uniformly spaced and arranged in a radial pattern about center point CP. Channels 910 are fluidically coupled with port 414-2 via manifold 912-2.

Fluidic networks 904-1 and 904-2 are analogous to microfluidic networks 404-1 and 404-2 described above, and filled with conductive fluid 416. As a result, each set of adjacent channels 908 and 910 function as the electrodes of an electrostatic actuator 916, which is analogous to electrostatic actuators 424 discussed above.

In the depicted example, muscle 900 also includes optional aperture 914, which runs through body 902 and is centered on center point CP. In the nascent state of muscle 900, aperture 914 has a nascent circumference.

In analogous fashion to electrostatic actuator 424, when a voltage is applied between contact pads 418-1 and 418-2, an attractive force is generated between each adjacent set of channels 408 and 410.

In contrast to the linear force (i.e., tension) collectively generated by electrostatic actuators 424, however, the compressive force generated by each electrostatic actuator 916 is directed circumferentially such that they collectively generate a constrictive force about center point CP (much like a rubber band around a rolled-up newspaper provides a constrictive force along the circumference of its loop, which squeezes the paper inward while also attempting to shrink the rubber band radially).

In some embodiments, this constrictive force gives rise to a reduction in the circumference of aperture 914, which can be advantageously used in numerous applications. For example, if aperture 914 were to surround a portion of a fluidic channel, the constrictive force could be used to create a pressure wave in the fluid within the channel. A plurality of muscles 900 operated in such a manner could be used as a peristaltic pump. In some cases, aperture 914 could be closed nearly completely, mimicking the behavior of a biological sphincter muscle. It should be noted that sphincter-like operation can also be achieved using by wrapping a linear muscle fiber (e.g., fiber 400) in a helix about an element (e.g., a tube, etc.) and actuating it.

In some embodiments, muscle 900 does not include aperture 914 and/or muscle 900 is non-planar, which enables a variety of functions, such as peristaltic propulsion, volumetric compression, and the like.

It should be noted that the microscopic scale of the individual muscle fibers lands itself very well to building super-arrays of muscle fiber bundles that can substantially mimic the anatomic structure of human and animal muscles, locomotion, and/or propulsion systems. For example, ideally, a biomimetic prosthetic limb or biomimetic-powered exoskeletal limb that has a range of motion, degrees of freedom, and intuitive use that approximates the original limb it replaces is highly desirable. Such a prosthetic device is possible within the scope of the present disclosure via arrangements of muscle fibers in orientation, arrangements, and suspension points to the artificial endoskeleton or exoskeleton that are substantially anatomically correct. In other words, muscle fibers and muscles in accordance with the present disclosure lend themselves to virtually "verbatim" biomimetics, with significant advantages over prior-art artificial muscles with respect to fidelity and range of motions, as well as wearability and ease of use. Moreover, fabrication of artificial muscles in accordance with the present disclosure using 3D printing enables low-cost direct printing of monolithic 3D artificial muscles with the exact biomimetic structure necessary, thereby avoiding complex design, assembly, and optimization procedures.

It should be further noted that the ability to substantially mimic a biological muscle system, such as those of fish, etc., enables the application of muscles and/or muscle fibers in accordance with the present disclosure to many important applications, such as biomimetic propulsion of unmanned underwater vehicles (UUV) and unmanned surface vehicles (USV). For example, vehicles that propel themselves by mimicking the motion of the fins of pelagic fish (e.g. sharks, tuna, etc.) have inherent advantages in preventing cavitation of rotary propellers and, therefore, would have acoustic signatures more closely matching biologicals than manmade vehicles. As a result, such propulsion could be provided in an energetically efficient way.

In some applications, muscles and/or muscle fibers in accordance with the present disclosure can be fabricated to match the anatomy of large walking animals, such as ostriches or large cats, thereby offering more optimized land locomotion with different objectives. For example, ostrich-like limbs on ground vehicles offer the potential for maximizing cross-country access and large ground clearance (e.g., for anti-mine and anti-IED (improvised explosive devices) stratagem, etc.). Furthermore, in some applications, large-cat-like limbs offer the potential for high speed and jumping capability in a ground vehicle, which would be highly useful in families of scout vehicles, robots, armored personnel carriers with multiple pairs of limbs, and the like. It can also enable improved protection against enemy fire or explosive devices, since a multi-limbed vehicle would not be totally disabled by the loss of some of its limbs—in contrast to four-wheel ground vehicles that are disabled by the loss of a single wheel, or a tracked vehicle that can be disabled by the loss of one track.

It is to be understood that the disclosure teaches only examples of embodiment in accordance with the present disclosures and that many variations of these embodiments can easily be devised by those skilled in the art after reading this disclosure and that the scope of the present invention is to be determined by the following claims.

What is claimed is:

1. A method for forming an artificial muscle, the method comprising:
   forming a body that comprises a first material that is a dielectric elastomer, wherein the body includes (1) a first microfluidic network that includes a first plurality of channels and a first manifold that is fluidically coupled with each channel of the first plurality thereof and (2) a second microfluidic network that includes a second plurality of channels and a second manifold that is fluidically coupled with each channel of the second plurality thereof, wherein the first microfluidic network and second microfluidic network are arranged such that the channels of the first plurality thereof and the channels of the second plurality thereof are interdigitated and spaced apart;
   filling the first microfluidic network with a second material that is electrically conductive, wherein the second material is selected from the group consisting of a liquid and a gel; and
   filling the second microfluidic network with the second material.

2. The method of claim 1 wherein the body is formed by operations comprising:
   defining a first shape that includes the first microfluidic network;
   defining a second shape that includes the second microfluidic network;
   forming a first sacrificial element having the first shape;
   forming a second sacrificial element having the second shape;
   forming a nascent body that comprises the first material, wherein the nascent body encloses a portion of each of the first and second sacrificial elements; and
   removing the first and second sacrificial elements.

3. The method of claim 2 wherein the nascent body is formed by operations comprising:
   forming a first portion of the nascent body on a substrate, the first portion comprising the first material; and
   forming a second portion of the nascent body over the portion of each of the first and second sacrificial elements, the second portion comprising the first material.

4. The method of claim 1 wherein the body is formed by three-dimensional (3D) printing of the first material.

5. The method of claim 4 wherein the body is formed by operations comprising:
   defining a first shape that includes the first microfluidic network;
   defining a second shape that includes the second microfluidic network;
   forming a first sacrificial element having the first shape, wherein the first sacrificial element is formed by 3D printing of a third material;
   forming a second sacrificial element having the second shape, wherein the second sacrificial element is formed by 3D printing of the third material;
   forming the body such that it encases a portion of each of the first and second sacrificial elements; and
   removing the third material.

6. A method for forming an artificial muscle, the method comprising:
   forming a first sacrificial element having a first shape that is based on a first microfluidic network, the first sacrificial element comprising a first material;
   forming a second sacrificial element having a second shape that is based on a second microfluidic network, the second sacrificial element comprising the first material;
   forming a body such that it encases a portion of each of the first and second sacrificial elements, the body comprising a second material that is resilient;
   removing the first material to define the first and second microfluidic networks within the body; and
   filling each of the first and second microfluidic networks with a third material that is electrically conductive, wherein the third material is selected from the group consisting of a liquid and a gel.

7. The method of claim 6 further electrically each of the first and second microfluidic networks with a voltage source.

8. The method of claim 6 wherein the first and second sacrificial elements are formed by 3D printing of the first material.

9. The method of claim 6 wherein the body is formed by 3D printing of the second material.

10. The method of claim 6 wherein second material is a dielectric elastomer.

11. The method of claim 6 wherein the first microfluidic network includes a first plurality of channels and a first manifold that is fluidically coupled with each channel of the first plurality thereof, and wherein the second microfluidic network includes a second plurality of channels and a second manifold that is fluidically coupled with each channel of the second plurality thereof, and further wherein the first microfluidic network and second microfluidic network are arranged within the body such that the channels of the first plurality thereof and the channels of the second plurality thereof are interdigitated and spaced apart.

12. The method of claim 6 wherein the body is formed by operations comprising:
   forming a first portion of the body on a substrate, the first portion comprising the second material;
   disposing the first and second sacrificial elements on the first portion; and
   forming a second portion of the body over at least some of the first and second sacrificial elements.

13. The method of claim 12 wherein the first material is a photoresist.

\* \* \* \* \*